US005725508A

United States Patent [19]
Chanoch et al.

[11] Patent Number: 5,725,508
[45] Date of Patent: Mar. 10, 1998

[54] QUICK CONNECT MEDICATION DELIVERY PEN

[75] Inventors: Lawrence H. Chanoch, Mahwah; John B. Wilson, Wanaque, both of N.J.

[73] Assignee: Becton Dickinson and Company, Franklin Lakes, N.J.

[21] Appl. No.: 314,179

[22] Filed: Sep. 28, 1994

Related U.S. Application Data

[63] Continuation-in-part of Ser. No. 263,591, Jun. 22, 1994.
[51] Int. Cl.$^6$ ............................................. A61M 5/00
[52] U.S. Cl. ........................... 604/207; 604/211; 604/232
[58] Field of Search .................................. 604/207, 208, 604/218, 211, 232, 152, 131, 182

[56] References Cited

U.S. PATENT DOCUMENTS 4,592,745  6/1986  Rex et al. ............................. 604/211
5,279,585  1/1994  Balkwill ............................... 604/207
5,549,575  8/1996  Giambahista et al. ............... 604/232

Primary Examiner—Michael Buiz
Assistant Examiner—At Nguyen
Attorney, Agent, or Firm—Alan W. Fiedler

[57] ABSTRACT

A medication delivery pen is provided having a reusable pen body assembly and a disposable cartridge assembly that are threadedly engageable with one another. The disposable cartridge assembly includes a plunger and can releasably receive a needle cannula assembly. A portion of the pen body assembly projects into the cartridge holder assembly for driving the cartridge plunger distances that are selected in accordance with a desired dose of medication to be delivered. The cartridge holder assembly can be disassembled from the pen body assembly after the medication therein has been exhausted, and the used cartridge holder assembly may be discarded and replaced.

6 Claims, 7 Drawing Sheets

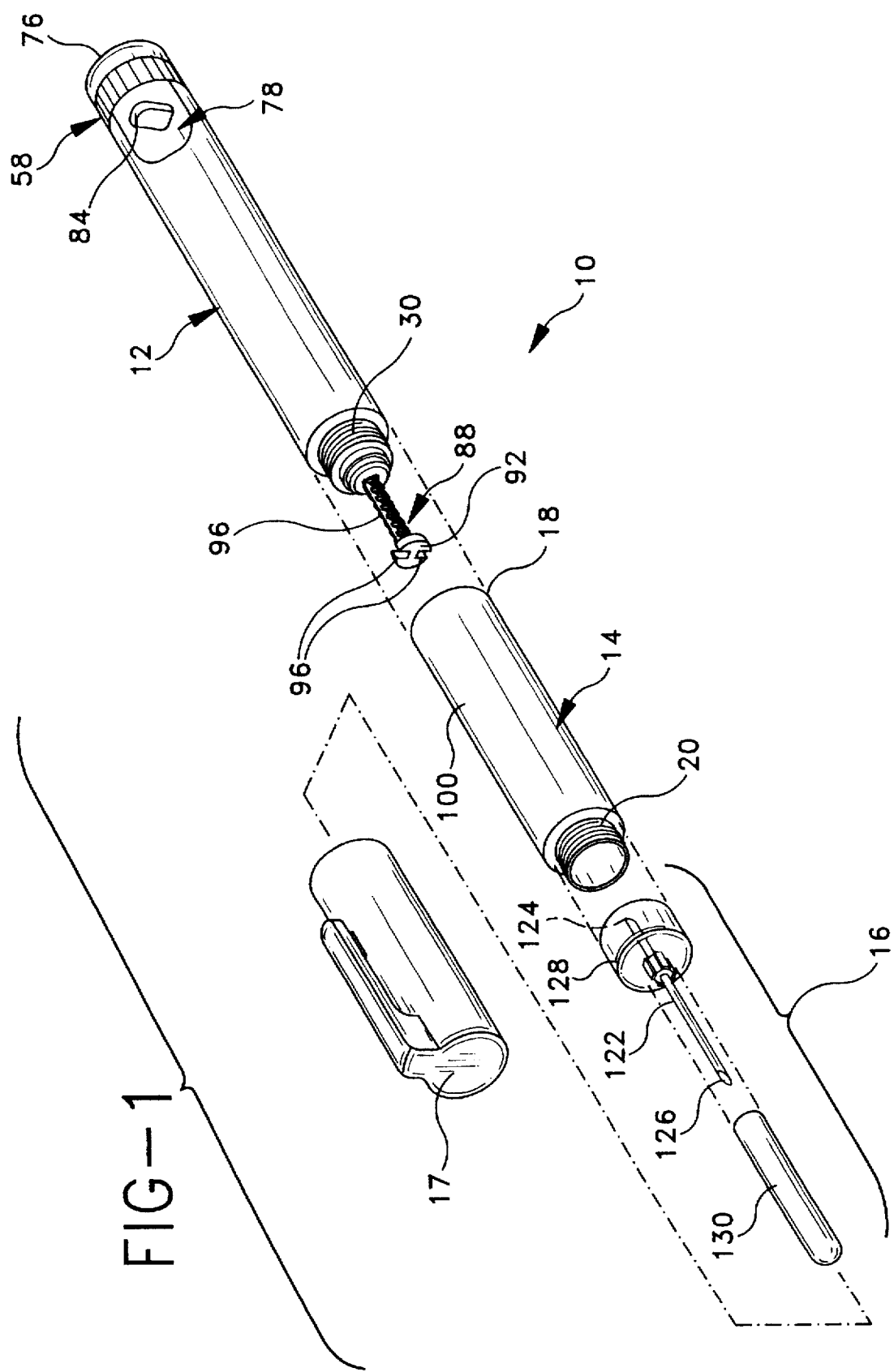

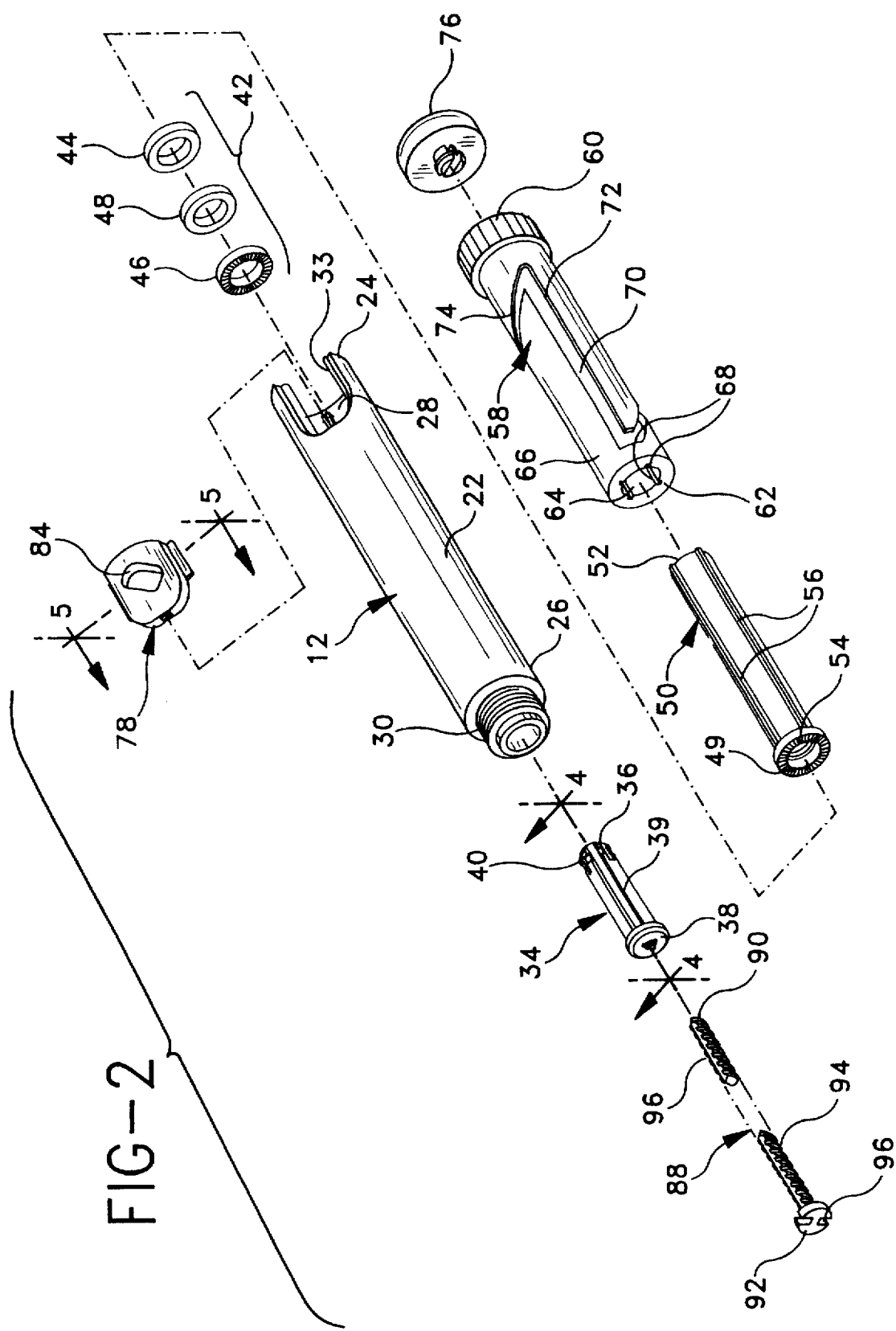

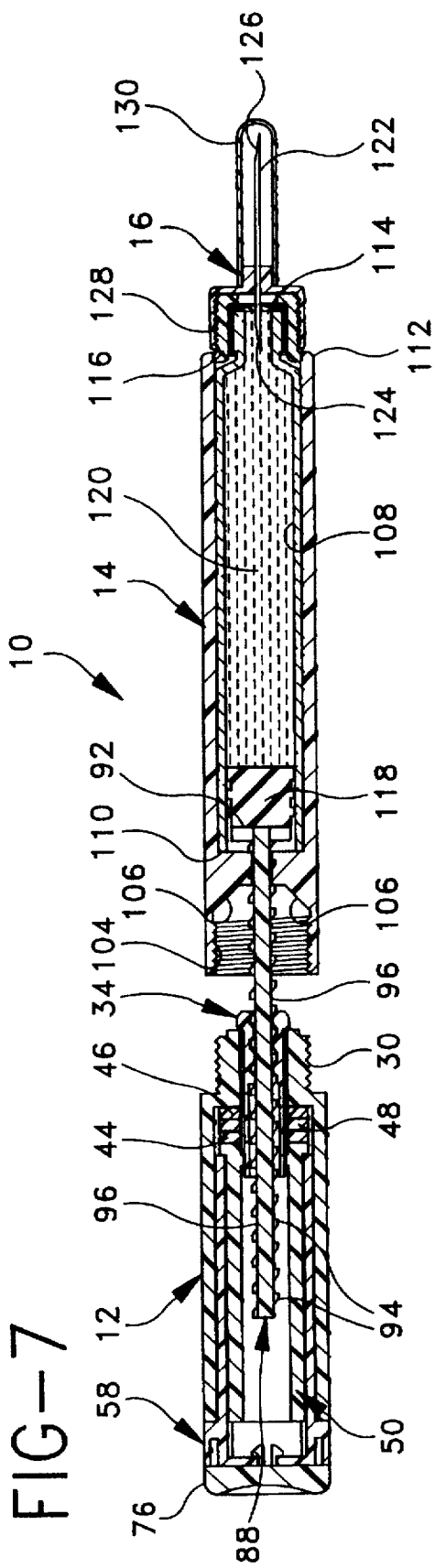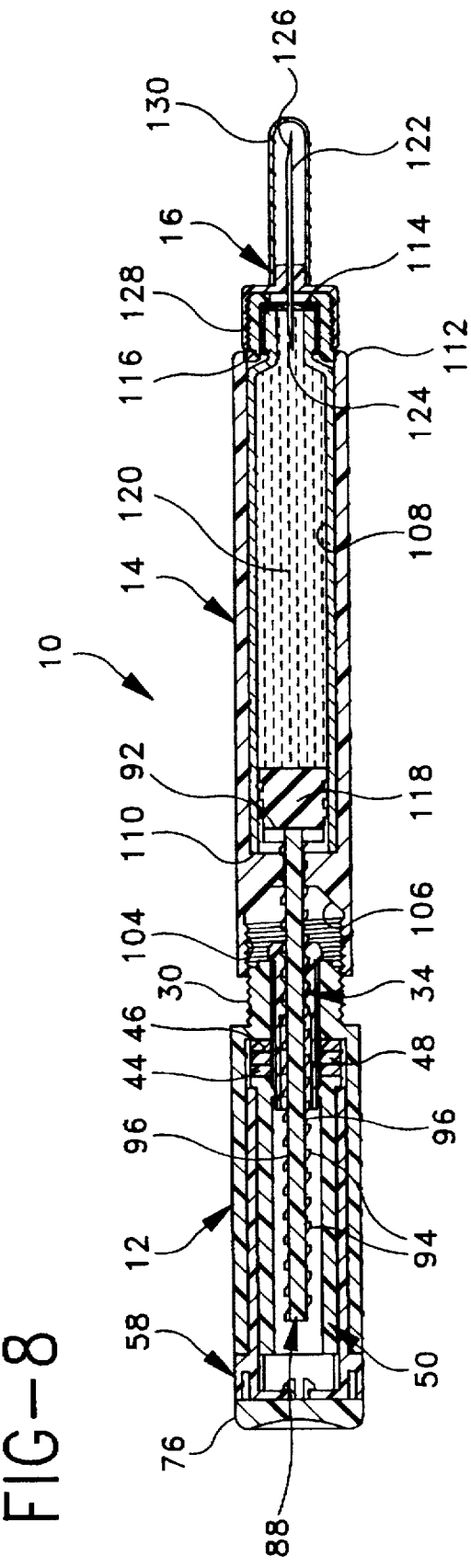

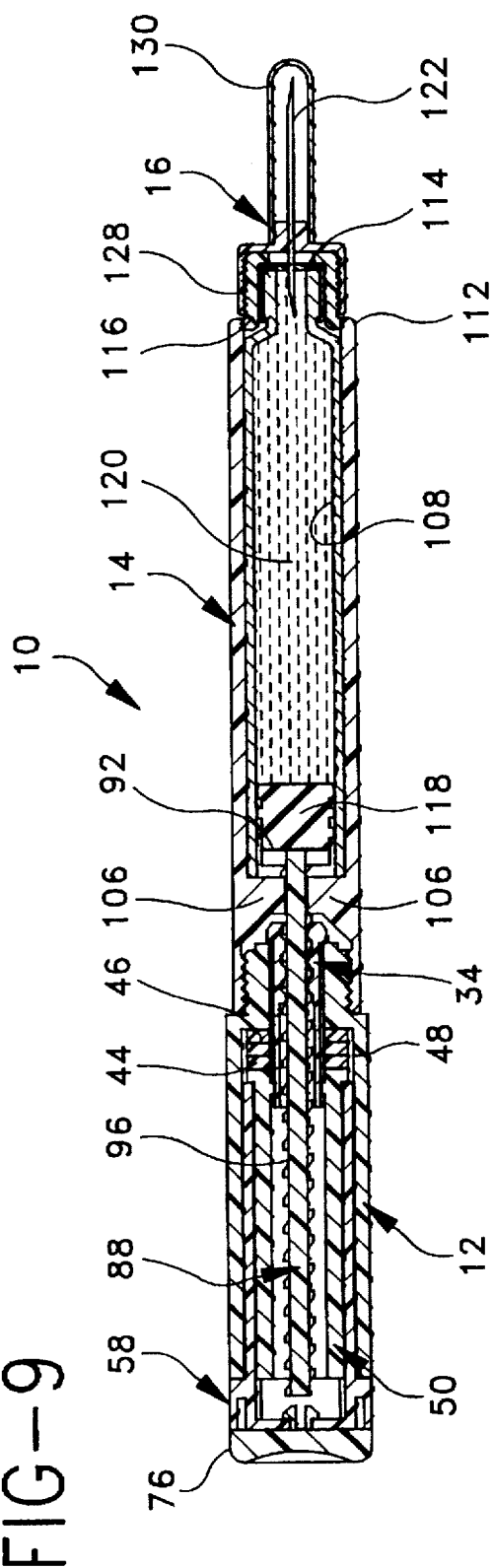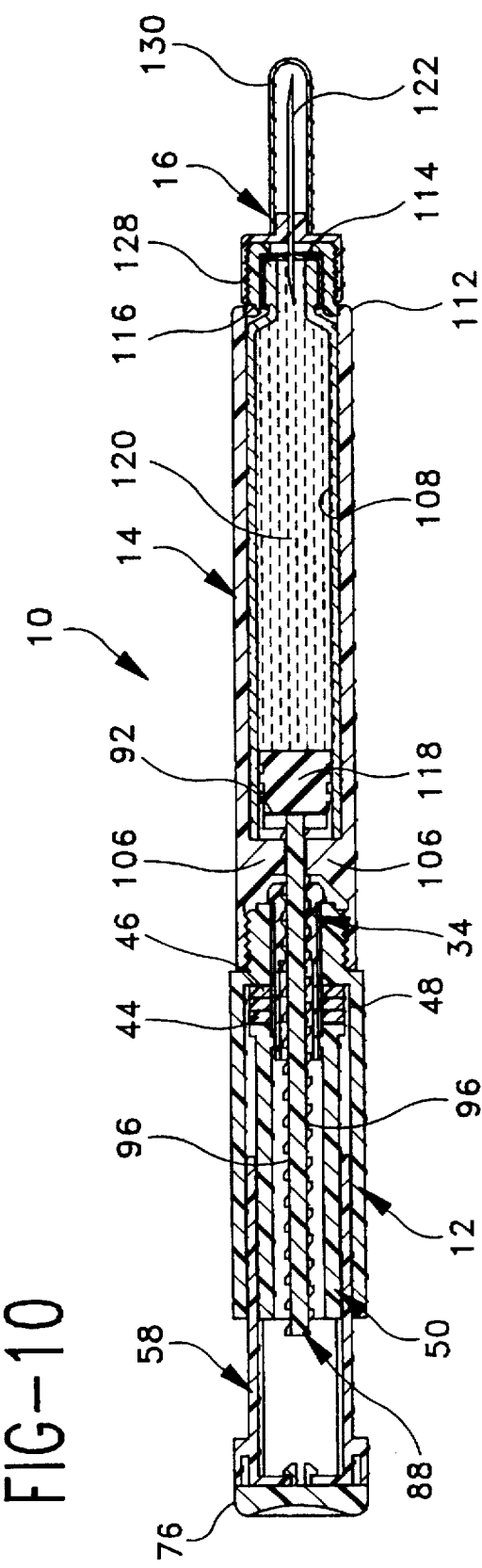

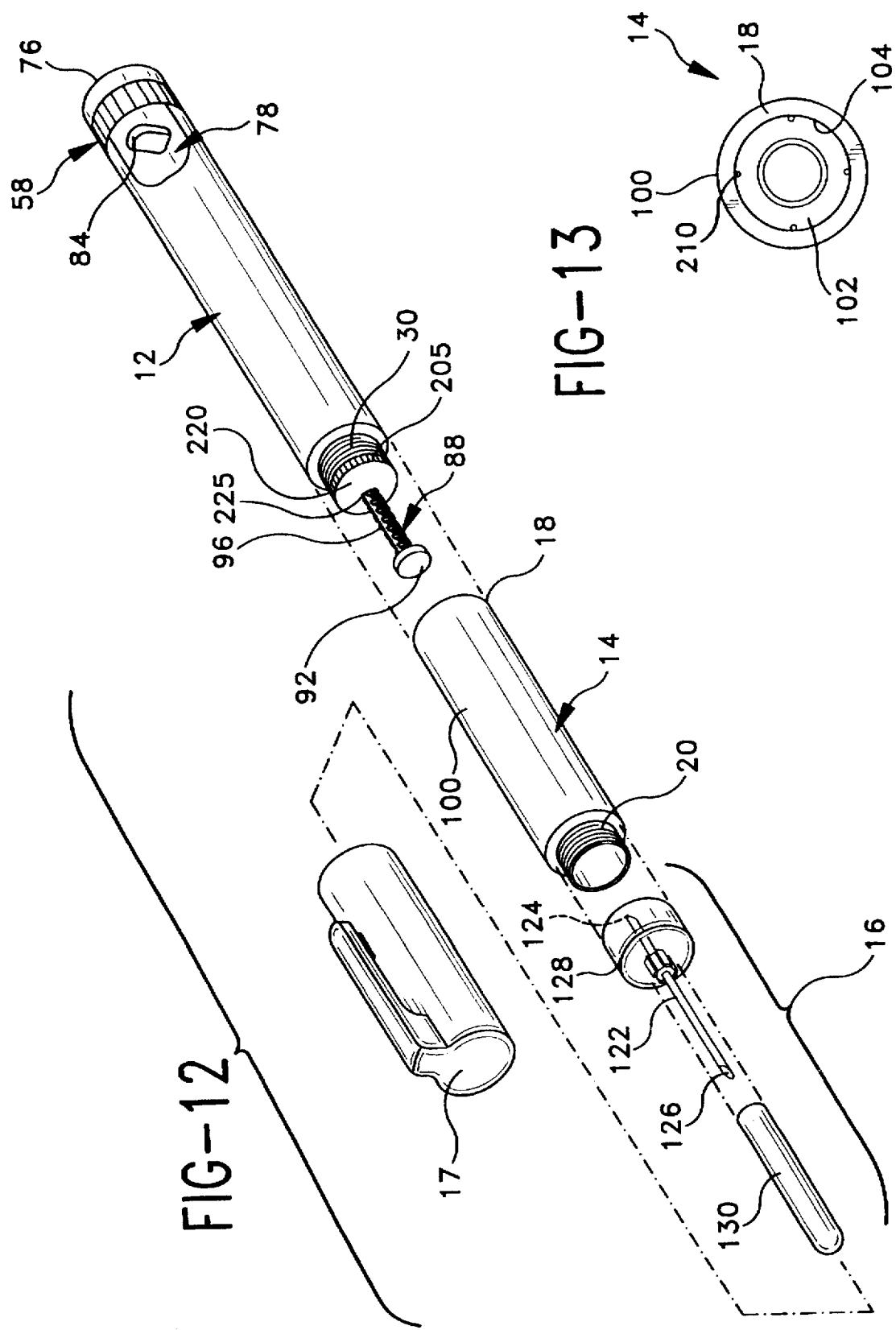

QUICK CONNECT MEDICATION DELIVERY PEN

This application is a continuation-in-part of application Ser. No. 08/263,591, filed on Jun. 22, 1994.

BACKGROUND OF THE INVENTION

1. Field of the Invention

The subject invention relates to medication delivery pens having a disposable cartridge holder assembly and a reusable pen body assembly removably mounted to the cartridge holder assembly for delivering selected doses of medication.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber.

A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described reusable medication delivery pen is effective and much more convenient for self-administration of medication than the typical hypodermic syringe and separate medication vial. However, the disassembly of the pen to remove empty medication vials and to insert new ones is an inconvenience. As a result, disposable pens have been developed. The prior art disposable medication delivery pen includes a vial of insulin or other such medication permanently encapsulated therein. The patient need merely connect a double-ended needle cannula to the disposable pen for each administration of medication. The prior art disposable pen can be discarded when the supply of medication permanently encapsulated therein has been exhausted.

Disposable medication delivery pens offer certain conveniences to the patient who is required to self-administer medication. However, the dose selecting and driving mechanisms of prior art medication delivery pens are fairly complex devices that are costly to manufacture. Hence, a substantial cost penalty is associated with the convenience of using a disposable medication delivery pen.

SUMMARY OF THE INVENTION

The subject invention relates to a medication delivery pen having a disposable medication cartridge assembly that is selectively engageable with and disengageable from a reusable pen body assembly. The disposable medication cartridge assembly is an elongate generally cylindrical structure having opposed proximal and distal ends. The distal end of the disposable medication cartridge assembly includes needle mounting means for securely but releasably receiving a needle cannula assembly. The distal end may be characterized by a pierceable elastomeric seal that may be repeatedly and reseatable pierced by the proximal end of a double-ended needle cannula. The proximal end of the disposable medication cartridge assembly includes body mounting means for securely but releasably mounting the disposable medication cartridge assembly to the reusable pen body assembly. The body mounting means may comprise an array of threads extending distally from the proximal end of the disposable medication cartridge assembly.

The disposable medication cartridge assembly further includes plunger means slidably disposed in fluid tight engagement therein. The plunger means may initially be disposed in a proximal position within the medication cartridge assembly and may be moved in a distal direction by a driver projecting from the pen body assembly. The disposable medication cartridge assembly further comprise anti-rotation means for preventing rotation of the driver.

The reusable pen body assembly of the subject invention comprises an array of mounting threads to enable threaded engagement of the reusable pen body assembly and the disposable medication cartridge assembly. An actuator button may be rotatably mounted on the proximal end of the pen body assembly. Thus, axial forces exerted on the actuator button will cause the pen body assembly to threadedly engage the disposable medication cartridge assembly.

The pen body assembly further includes a lead screw for selectively engaging the plunger of the disposable cartridge assembly and for urging the plunger of the disposable cartridge assembly in a distal direction. At least a portion of the lead screw may have driving threads engaged with other portions of the pen body assembly. This threaded engagement may be operative to achieve axial movement of the lead screw in response to axial forces exerted on the rotatable actuator button. The driving threads may define the same pitch and the same direction of generation as the mounting threads of the pen body assembly. As will be explained in greater detail below, this feature of the medication delivery pen facilitates the quick connection of the pen body assembly to the disposable medication cartridge assembly, and further assures a virtually automatic return of the lead screw to a start position each time a new disposable medication cartridge assembly is mounted to the pen body assembly. The lead screw may further be engageable with the anti-rotation means of the disposable cartridge assembly. Thus, relative rotation between the lead screw means and the disposable cartridge assembly is substantially prevented.

The pen body assembly further comprises a dose setting means for establishing and precisely controlling the amount of medication to be delivered in response to each actuation of the actuator button. The dose setting means may be any of several structures as described in greater detail below.

A disposable cartridge assembly that is filled with medication may be mounted to the pen body assembly by merely aligning the lead screw with the proximal end of the disposable cartridge assembly and exerting an axial force on the rotatable actuator button. The initial response to forces on the actuator button will cause the lead screw to move in a proximal direction toward its starting position, while the remaining portions of the pen body assembly move distally toward the disposable vial assembly. Further forces exerted on the actuator button will cause the mounting means of the pen body to engage the mounting means of the disposable cartridge assembly. Continued axial forces on the actuator will cause the mounting threads to engage the disposable cartridge assembly and will continue the proximal movement of the driver. The pen body assembly will be fully but releasably engaged with the disposable cartridge assembly at the same time that the driver is at its proximal extreme position and in condition to begin delivering selected doses of medication from the pen. Doses of medication can be dispensed as needed over time. The disposable cartridge assembly can be removed and discarded when the medication therein has been exhausted, and a new disposable medication cartridge assembly may be mounted to the pen body assembly as described above.

DESCRIPTION OF THE DRAWINGS

FIG. 1 is an exploded perspective view of the medication delivery pen of the subject invention.

FIG. 2 is an exploded perspective view of the pen body assembly of the medication delivery pen shown in FIG. 1.

FIG. 7 is a longitudinal cross-sectional view of the pen in a first partly assembled condition.

FIG. 8 is a cross-sectional view similar to FIG. 7, and showing the pen in a second partly assembled condition.

FIG. 9 is a cross-sectional view similar to FIGS. 7 and 8, and showing the pen in a fully assembled condition.

FIG. 10 is a cross-sectional view similar to FIG. 9, and showing the assembled pen in condition to deliver a selected dose of medication.

FIG. 12 is an exploded perspective view of an alternative embodiment of a medication delivery pen of the subject invention.

FIG. 13 is an end elevational view of the cartridge assembly in the medication delivery pen shown in FIG. 12.

DETAILED DESCRIPTION

Figure 4:
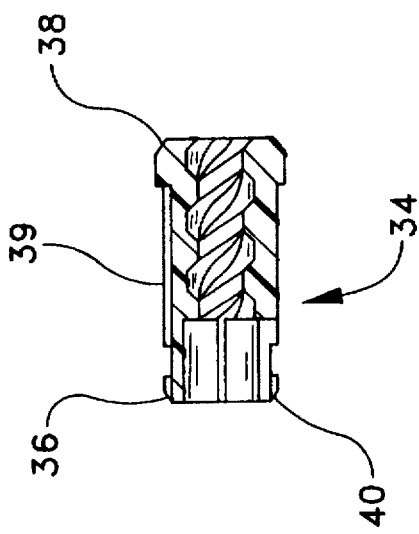
FIG. 4 is a cross-sectional view of the nut taken along line 4—4 in FIG. 2.
Figure 6:
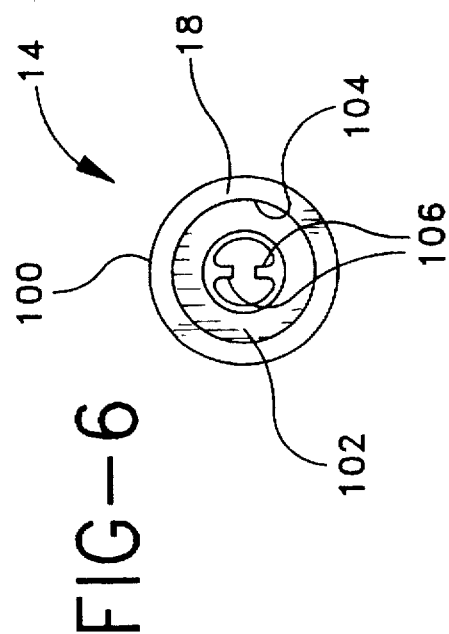
FIG. 6 is an end elevational view of the cartridge holder assembly.

A medication delivery pen in accordance with the subject invention is identified generally by the numeral 10 in FIGS. 1 and 7–11. Medication delivery pen 10 includes a reusable pen body assembly 12, a disposable cartridge assembly 14, a needle cannula assembly 16 and a cap 17. Cartridge assembly 14 includes opposed proximal and distal ends 18 and 20 respectively. Proximal end 18 of cartridge assembly 14 is dimensioned and configured to threadedly engage pen body assembly 12, as explained further herein. Distal end 20 of cartridge assembly 14 is configured to securely but releasably engage needle cannula assembly 16.

Figure 3:
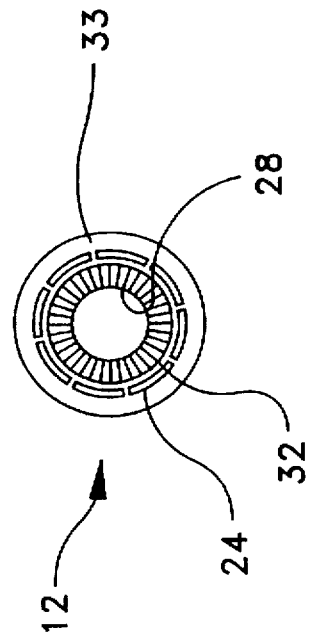
FIG. 3 is an end view of the housing of the pen body assembly.
Figure 5:
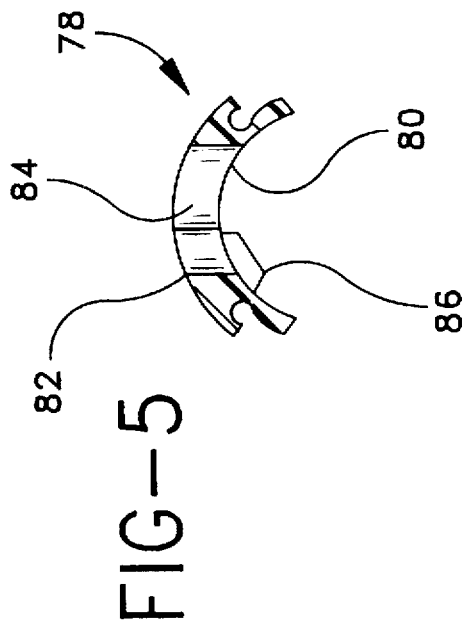
FIG. 5 is a cross-sectional view of the insert taken along line 5—5 in FIG. 2.

The preferred embodiment of reusable pen body assembly 12 is illustrated in greater detail in FIG. 2. It is understood, however, that variations from this preferred embodiment may be provided, and are considered to be within the scope of the subject invention. Reusable pen body assembly 12 includes a generally cylindrical housing 22 having opposed proximal and distal ends 24 and 26, and a substantially hollow throughbore 28 extending axially therethrough. An array of external threads 30 extends proximally from distal end 26 for threaded engagement with proximal end 18 of cartridge holder assembly 14. Portions of hollow throughbore 28 of housing 22 adjacent distal end 26 are characterized by an array of clutch teeth 32, shown in FIG. 3, molded therein. Proximal end 24 of housing 22 is characterized by a cut-out 33 formed therein for receiving a window insert 78, as shown in FIG. 5 and explained further herein.

Pen body assembly 12 further includes a nut 34 having opposed proximal and distal ends 36 and 38 respectively.

Exterior surface regions of nut 34 between proximal and distal ends 36 and 38, shown in FIG. 4, define a plurality of longitudinally extending splines 39. Proximal end 36 of nut 34 is characterized by a plurality of longitudinally extending resilient fingers 40 with enlarged ends that enable snap engagement of nut 34 into other portions of pen body assembly 12 as explained further herein. Distal end 38 of nut 34 is radially enlarged to limit axial movement of nut 34 into distal end 26 of housing 22. Thus, nut 34 is axially constrained within housing 22. However, the dimensions and configurations of nut 34 and housing 22 permit free relative rotation therebetween.

Pen body assembly 12 further includes a clutch assembly 42 mounted therein. Clutch assembly 42 includes a proximal clutch 44, a distal clutch 46 and an annular spring 48 biasingly engaged therebetween. Proximal and distal clutches 44 and 46 each are configured for non-rotatable engagement over splines 39 of nut 34. Distal clutch 46 includes an array of distally facing saw teeth dimensioned, disposed and configured for engagement with teeth 32, shown in FIG. 3, on the interior of housing 22, such that distal clutch 46 can rotate only in one direction relative to housing 22. Proximal clutch 44 includes an array of proximally facing teeth which are also configured for unidirectional rotation as explained further herein.

Pen body assembly 12 further includes a generally cylindrical driver 50 having opposed proximal and distal ends 52 and 54. Driver 50 is slidably inserted into housing 22 of pen body assembly 12 such that distal end 54 of driver 50 is snap fit over the enlarged ends of resilient fingers 40 at proximal end 36 of nut 34. This snap fit engagement prevents axial movement between nut 34 and driver 50, but permits free relative rotational movement within housing 22. Distal end 54 of driver 50 is also characterized by an array of saw teeth 49 that engage with the saw teeth on proximal clutch 44. Outer surface regions of driver 50 are characterized by splines 56 extending radially outwardly thereon and along a substantial portion of the length of driver 50.

Pen body assembly 12 further includes a dose knob 58 which is a hollow generally cylindrical structure having opposed proximal and distal ends 60 and 62 and opposed inner and outer surfaces 64 and 66. Inner surface 64 is characterized by longitudinally extending grooves 68 which are disposed and dimensioned for engagement with splines 56 on driver 50. More particularly, dose knob 58 is spline mounted over driver 50 within housing 22 of pen body assembly 12. Thus, axially extending grooves 68 in dose knob 58 engage splines 56 of driver 50 to prevent relative rotation therebetween, but permitting relative axial movement. Outer surface 66 of dose knob 58 is characterized by a groove 70 that includes a linear component 72 and a helical component 74, which connects opposed ends of linear component 72. Portions of outer surface 66 adjacent helical component 74 of groove 70 are provided with dosage indicia to define dose amounts corresponding to different positions along groove 70 as explained further herein. Proximal end 60 of dose knob 58 is characterized by a gnarled exterior surface to facilitate manipulation for setting a selected dose. An actuator button 76 is snapped in to engagement with proximal end 60 of dose knob 58 to permit relative rotation therebetween.

An insert 78, shown in FIGS. 2 and 5, is snapped into engagement with cut-out 33 in the proximal end 24 of housing 22. Insert 78 includes opposed inner and outer surfaces 80 and 82 and a window 84 extending therebetween. Inner surface 80 of insert 78 includes a button 86 on an interior face which is dimensioned and disposed to engage in groove 70 of dose knob 58. Button 86 and window 84 are disposed to enable the indicia on dose knob 58 to be visible through window 84.

Pen body assembly 12 further includes a lead screw 88 with opposed proximal and distal ends 90 and 92 and an array of external threads 94. External threads 94 are characterized, however, by a pair of opposed axially extending grooves 96 which extend from distal end 92 substantially to the proximal end 90. Threads 94 are engaged in nut 34, such that proximal end 90 of lead screw 88 is within housing 22 and distal end 92 projects distally beyond housing 22. Threads 94 on lead screw 88 have exactly the same pitch and the same hand as threads 30 on distal end 26 of housing 22.

Pen body assembly 12 is assembled by placing nut 34 into housing 22 from distal end 26. Clutch assembly 42 then is mounted over splines 39 on nut 34. Driver 50 is then inserted into proximal end 24 of housing 22, and is urged sufficiently in a distal direction for snap fit engagement with nut 34. In this snapped engagement, the saw teeth of distal clutch 46 will be secured in engagement with teeth 32 of housing 22, and the saw teeth of proximal clutch 44 will be engaged with saw teeth 49 at distal end 54 of driver 50. Spring 48 will maintain constant selected pressure between these interengaged saw teeth. Insert 78 then is positioned over dose knob 58 such that button 86 of insert 78 is engaged in the axial return track 72 of groove 70 in dose knob 58. The temporarily assembled insert 78 and dose knob 58 then are urged into housing 22. Lead screw 88 then is threaded into nut 34, and actuator button 76 is snapped into engagement with proximal end 60 of dose knob 58.

Cartridge assembly 14, shown in FIGS. 1 and 6–11, includes a molded housing 100 which extends from proximal end 18 to distal end 20 of cartridge assembly 14, as noted above. Housing 100 includes a mounting cavity 102 extending inwardly from proximal end 18. Mounting cavity 102 is characterized by an array of internal threads 104 for threaded engagement with external threads 30 on distal end 26 of housing 22. The distal end of mounting cavity 102 is defined by anti-rotation tabs 106 which are dimensioned to slidably engaged in slots 96 of lead screw 88. Thus, lead screw 88 can slidably move relative to anti-rotation tabs 106, but is prevented from rotating relative to tabs 106.

Cartridge holder assembly 14, as shown in FIGS. 7–11, further includes a medication cartridge 108 securely retained in housing 100 between tabs 106 and distal end 20 of cartridge assembly 14. Medication cartridge 108 includes an open proximal end 110 and a distal end 112 having a pierceable elastomeric seal 114 securely mounted thereto. A cap 116 extends between housing 100 and cartridge 108 for securely and permanently holding medication cartridge 108 in housing 100. A plunger 118 is disposed in sliding fluid tight engagement in cartridge 108. As shown in FIGS. 7–11, plunger 118 initially is disposed substantially adjacent proximal end 110 of medication cartridge 108. Portions of cartridge 108 between plunger 118 and seal 114 are filled with a medication 120, such as insulin.

Needle cannula assembly 16 includes a double ended needle cannula 122 having opposed proximal and distal points 124 and 126, respectively, and a lumen extending axially therebetween. A mounting hub 128 is engaged on needle cannula 122 and is removably engageable with cap 116 of cartridge holder assembly 14. The relative location of mounting hub 128 ensures that proximal point 124 of needle cannula 122 will pierce seal 114 when mounting hub 128 is engaged with cap 116. Needle cannula assembly 16 further includes a shield 130 removably mounted thereon for protecting against accidental needle sticks until immediately prior to use of pen 10.

As noted above, pen body assembly 12 is reusable, and cartridge holder assembly 14 is disposable. More particularly, cartridge 108 in cartridge holder assembly 14 will contain a volume of medication 120 sufficient for administration of several doses. After exhaustion of the medication 120, cartridge holder assembly 14 will be threadedly disengaged from pen body assembly 12 and discarded. A new cartridge holder assembly 14 may then be mounted to the reusable pen body assembly 12. To effect the mounting of a new cartridge holder assembly 14 to the reusable pen body assembly 12, the patient need merely align slots 96 at distal end 92 of lead screw 88 with tabs 106 at proximal end 18 of cartridge holder assembly 14. Distal end 92 of lead screw 88 is then advanced distally into cartridge holder assembly 14 until distal end 92 of lead screw 88 engages plunger 118, as shown in FIG. 7. Assembly continues by merely exerting axial forces on thumb swivel 76 and on cartridge holder assembly 14. Additionally, friction between plunger 118 and cartridge 108 and fluid forces exerted by medication 120 and seal 114 will prevent axial advancement of lead screw 88 beyond the position depicted in FIG. 9 during assembly. Additionally, the splined engagement of distal clutch 46 with nut 34 and the engagement of the teeth on distal clutch 46 with the corresponding teeth 32 on housing 22 prevents independent rotation of nut 34 during this initial mounting of reusable pen body assembly 12 with a new disposable cartridge assembly 14. Thus, axial forces exerted on thumb swivel 76 will cause cartridge housing 100 to threadedly advance along threads 94 of lead screw 88.

After sufficient axial advancement, threads 30 at distal end 26 of pen body housing 22 will engage internal threads 104 at proximal end 18 of cartridge holder assembly 14, as shown in FIG. 8. As noted above, external threads 30 at distal end 26 of housing 22 have exactly the same pitch and hand as threads 94 on lead screw 88. Hence, further axial forces exerted on thumb swivel 76 will cause the simultaneous threaded advancement of housing 22 along lead screw 88 and into cavity 102 at proximal end 18 of cartridge holder assembly 14. Thus, because of their identical pitches, lead screw 88 will move proximally relative to pen body housing 22, while pen body housing 22 and cartridge holder assembly 14 are approaching their fully seated and threaded condition depicted in FIG. 9.

The assembled reusable pen body assembly 12 and cartridge assembly 14 may be stored until a selected dose of medication is required. Just prior to use, a needle cannula assembly 16 may be threadedly engaged to distal end 20 of cartridge assembly 14. This threaded engagement will cause proximal tip 124 of needle cannula 122 to pierce seal 114 and provide communication with medication 120. Shield 130 may then be removed.

A desired dose of medication 120 may be set by rotating dose knob 58 until indicia corresponding to the desired dose appears in window 84 of insert 78. The engagement of button 86 on insert 78 in helical portion 74 of groove 70 in dose knob 58 will cause a threaded retraction of dose knob 58 relative to housing 22 of reusable pen body assembly 12. This threaded retraction of dose knob 58 will cause a simultaneous rotation of driver 50 splined thereto. However, nut 34 will not rotate because the saw teeth on distal clutch 46 and saw teeth 32 on interior portions of housing 22 are locked to prevent rotation in that direction. Proximal clutch 44 is splined to nut 34, and hence also will not turn. However, saw teeth 49 at distal end 54 of driver 50 are shaped to allow rotation relative to proximal clutch 44, but provide an audible click for each unit of medication in the selected dose. This is helpful for visually impaired patients who may be required to set doses and administer insulin or other medication to themselves. Annular spring 48 contributes to the engagement that provides these audible clicking sounds.

When the desired dose is set, as shown in FIG. 10, injection is achieved by merely pushing on actuator button 76. This causes dose knob 58 to turn about helix 74 relative to pen body housing 22, and driver 50 rotates through the same number of degrees. This rotation is opposite to the rotation generated by the dose setting procedure, and the rotational freedom of the clutch assembly 42 is reversed. Thus, as driver 50 turns the previously clicking proximal clutch 44 is locked to and turns with driver 50. This driving movement of proximal clutch 44 causes a corresponding rotational movement of nut 34 because of the splined engagement therebetween. Distal clutch 46 is now free to rotate against saw teeth 32 on housing 22, and makes an audible clicking indication during injection of medication.

Figure 11:
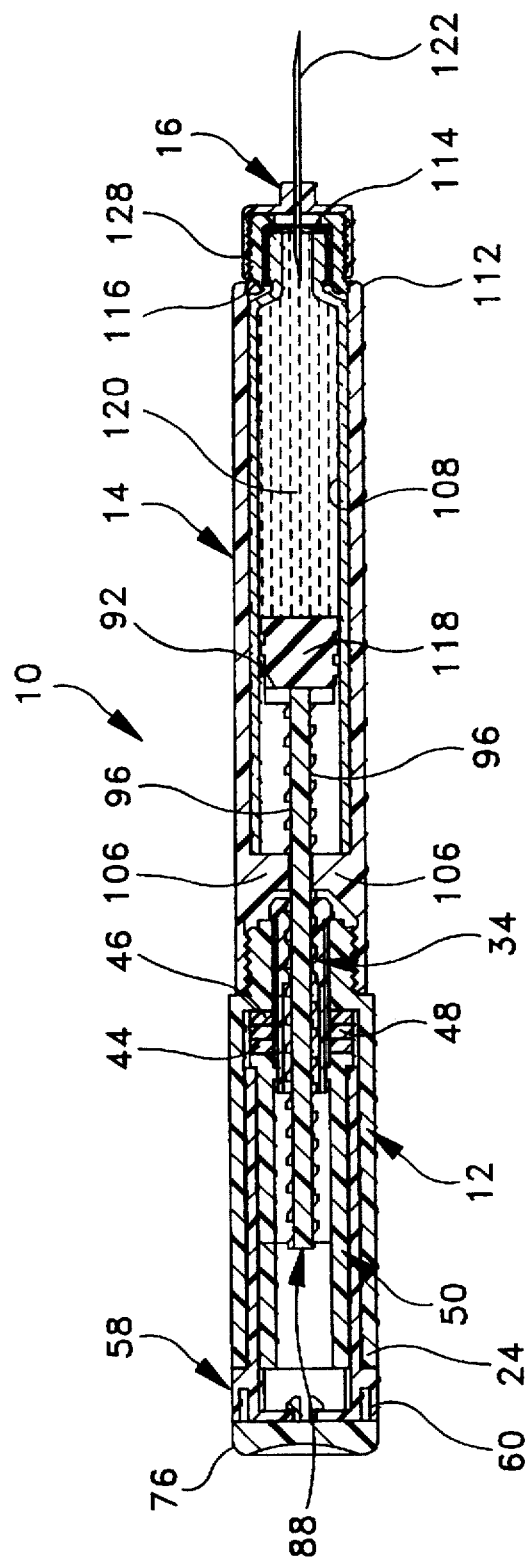
FIG. 11 is a cross-sectional view similar to FIG. 10 and showing the pen after delivery of the selected dose.

Rotation of lead screw 88 is prevented by tabs 106 unitarily molded with housing 100 of cartridge holder assembly 14. Therefore, as nut 34 rotates under the driving action of proximal clutch 44 and driver 50, lead screw 88 will be advanced axially into cartridge holder assembly 14. This axial advancement of lead screw 88 causes distal end 92 thereof to urge plunger 118 distally into cartridge 108, and hence causes medication 120 to be injected through needle cannula 122. Injection will be terminated when proximal end 60 of dose knob 58 engages against proximal end 24 of pen body housing 22, as shown in FIG. 11.

Upon completion of the injection, needle cannula assembly 16 may be disengaged from cartridge holder assembly 14 and safely discarded. Cap 17 may be mounted over cartridge holder assembly 14, and pen 10 may be stored or carried in a convenient location until the next dose of medication is required. A subsequent dose of medication will be set in exactly the manner as described above. However, for such a subsequent dose, lead screw 88 and plunger 118 will be in a partly advanced position as a starting point. Dose setting and injections can be carded out until all of medication 120 has been used. Cartridge holder assembly 14 may then be threadedly disengaged from pen body assembly 12, and slidably separated from lead screw 88. The separated cartridge holder assembly may then be discarded and replaced as described above.

FIG. 12 shows an alternative embodiment of a medication delivery pen 200 according to the present invention that does not include anti-rotation tabs 106 formed in mounting cavity 102 of cartridge holder assembly 14, like that shown in the medication delivery pen described above. As shown in FIGS. 12 and 13, cartridge holder assembly 14 of pen 200 includes a plurality of ribs 210 extending from the proximal end 18 of housing 100 into mounting cavity 102. Ribs 210 are disposed to slide over and prevent rotation of a rotatable disk 220 mounted upon pen body assembly 12. Disk 220 includes a textured circumference 205 such that each rib 210 meshes with a portion of the textured circumference 205 when cartridge holder assembly 14 is being mounted on pen body assembly 12. Disk 220 also includes a pair of tabs 225 that ride within slots 96 of lead screw 88 to prevent rotation of lead screw 88, when cartridge holder assembly 14 is being mounted on pen body assembly 12. The specific embodiment shown in FIGS. 12 and 13 is merely exemplary, a medication delivery pen according to the present invention could also function with only one slot in lead screw 88 for receiving only one tab 225. Likewise, it is not necessary for lead screw 88 to have a slot or disk 220 to have a tab, since lead screw 88 could merely have a flat portion extending along its side for mating with a flat portion within a hole in disk 220. All these variations would provide the benefits of the present invention and, more particularly, eliminate the need for slots 96 in distal end 92 of lead screw 88 and tabs 106 in proximal end 18 of housing 100 which would therefore permit standard medication cartridges to be used with the medication delivery pen.

While the invention has been described with respect to a preferred embodiment, it is apparent that various changes can be made without departing from the scope of the invention as defined by the appended claims. In particular, the reusable pen body assembly may have other driving and/or clutch mechanisms. Additionally, different means for preventing and/or enabling rotation during the dose setting and injection phases may be provided. Similarly, other means for mounting needle cannula to the cartridge assembly may be provided. These various optional constructions will be apparent to those skilled in the art after having read the subject disclosure.

What is claimed is:

1. A medication delivery pen comprising:

a disposable medication-containing cartridge having a plunger in sliding fluid tight engagement within said cartridge;

a cartridge assembly for holding said cartridge and having opposed proximal and distal ends with said proximal end having an array of threads;

a reusable pen body assembly for mounting on said cartridge assembly and including a housing with opposed proximal and distal ends, said distal end having an array of threads dimensioned and having a pitch for threaded engagement with said array of threads at said proximal end of said cartridge assembly;

a lead screw having a proximal end disposed in said housing and a distal end projecting beyond said distal end of said housing for selective engagement with said plunger to push said plunger in said distal direction, said lead screw having a plurality of threads extending between said proximal end and said distal end of said lead screw and having a pitch substantially equal to said pitch of said array of threads at said distal end of said housing; and anti-rotation means for preventing relative rotation between said lead screw and said housing when said housing is being threaded to said cartridge assembly, whereby said lead screw moves in a distal direction in said cartridge assembly as said housing is threadedly moved in a distal direction into said cartridge assembly, said anti-rotation means comprising:

a rotatable disk having a textured circumference that is mounted at said distal end of said housing to rotate with said lead screw; and a plurality of ribs in said cartridge assembly for mating with said textured circumference of said disk to prevent rotation of said lead screw when said housing is threaded to said cartridge assembly.

2. The medication delivery pen of claim 1, wherein said pen body assembly further includes driver means for driving said lead screw into said cartridge assembly and an actuator button rotatably mounted on said driver means, such that axial forces exerted on said actuator button simultaneously generate movement of said lead screw distally into said cartridge assembly.

3. The medication delivery pen of claim 1, wherein said cartridge assembly defines a mounting cavity adjacent said proximal end thereof, said plurality of threads of said cartridge assembly defining internal threads in said mounting cavity, said distal end of said housing being dimensioned for threaded engagement in said mounting cavity of said cartridge assembly.

4. The medication delivery pen of claim 1, wherein said pen body assembly comprises dose setting means for defining specified distances of travel for said lead screw corresponding to selected doses of medication to be delivered.

5. The medication delivery pen of claim 1, wherein said cartridge further comprises a sealed end having a pierceable elastomeric seal, said cartridge assembly further comprises needle mounting means at said distal end, and said medication delivery pen further comprises a needle cannula assembly having;

a hub selectively engageable with said mounting means of said cartridge assembly and a double-ended needle having opposed proximal and distal points, said proximal point of said needle being dimensioned and disposed to pierce said seal upon engagement with said cartridge.

6. The medication delivery pen of claim 1, wherein:

said rotatable disk includes a hole for receiving said lead screw and at least one tab extending into said hole; and said lead screw further includes at least one slot extending axially along said lead screw for receiving said tab to prevent rotation of said lead screw when said plurality of ribs are mated with said rotatable disk.

* * * * *